United States Patent
Johnston et al.

(10) Patent No.: US 9,724,358 B2
(45) Date of Patent: *Aug. 8, 2017

(54) MINOCYCLINE COMPOUNDS AND METHODS OF USE THEREOF

(71) Applicant: Paratek Pharmaceuticals, Inc., Boston, MA (US)

(72) Inventors: Sean M. Johnston, Doylestown, PA (US); Robert D. Arbeit, W. Newton, MA (US); Thomas J. Bigger, Norwell, MA (US); Dennis P. Molnar, Hopkinton, MA (US); S. Ken Tanaka, Needham, MA (US)

(73) Assignee: Paratek Pharmaceuticals, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/995,896

(22) Filed: Feb. 2, 2016

(65) Prior Publication Data

US 2016/0228459 A1 Aug. 11, 2016

Related U.S. Application Data

(63) Continuation of application No. 14/258,847, filed on Apr. 22, 2014, now Pat. No. 9,265,740, which is a continuation of application No. 12/398,980, filed on Mar. 5, 2009, now abandoned.

(60) Provisional application No. 61/068,180, filed on Mar. 5, 2008.

(51) Int. Cl.
*A61K 31/65* (2006.01)
*A61K 31/165* (2006.01)

(52) U.S. Cl.
CPC ............ *A61K 31/65* (2013.01); *A61K 31/165* (2013.01)

(58) Field of Classification Search
CPC ...................................................... A61K 31/65
USPC ........................................................ 514/152
See application file for complete search history.

(56) References Cited

U.S. PATENT DOCUMENTS

| | | | |
|---|---|---|---|
| 2,980,584 A | 4/1961 | Hammer | |
| 2,990,331 A | 6/1961 | Neumann et al. | |
| 3,062,717 A | 11/1962 | Hammer | |
| 3,165,531 A | 1/1965 | Blackwood et al. | |
| 3,454,697 A | 7/1969 | Joyner et al. | |
| 3,557,280 A | 1/1971 | Weber et al. | |
| 3,674,859 A | 7/1972 | Beutel et al. | |
| 3,957,980 A | 5/1976 | Noseworthy | |
| 4,018,889 A | 4/1977 | Armstrong | |
| 4,024,272 A | 5/1977 | Rogalski et al. | |
| 4,126,680 A | 11/1978 | Armstrong | |
| 4,806,372 A | 2/1989 | Strumskis | |
| 5,021,407 A | 6/1991 | Levy | |
| 5,258,372 A | 11/1993 | Levy | |
| 5,589,470 A | 12/1996 | Levy | |
| 5,811,412 A | 9/1998 | Levy | |
| 6,256,365 B1 | 7/2001 | Lai | |
| 6,500,812 B2 | 12/2002 | Nelson et al. | |
| 6,617,318 B1 | 9/2003 | Nelson et al. | |
| 6,624,168 B2 | 9/2003 | Nelson et al. | |
| 6,642,270 B2 | 11/2003 | Nelson et al. | |
| 6,683,068 B2 | 1/2004 | Nelson et al. | |
| 6,818,634 B2 | 11/2004 | Nelson et al. | |
| 6,818,635 B2 | 11/2004 | Nelson et al. | |
| 6,833,365 B2 | 12/2004 | Levy et al. | |
| 6,841,546 B2 | 1/2005 | Draper et al. | |
| 6,846,939 B2 | 1/2005 | Nelson et al. | |
| 6,849,615 B2 | 2/2005 | Nelson et al. | |
| 7,001,918 B2 | 2/2006 | Huss et al. | |
| 7,045,507 B2 | 5/2006 | Draper et al. | |
| 7,056,902 B2 | 6/2006 | Nelson et al. | |
| 7,067,681 B2 | 6/2006 | Nelson et al. | |
| 7,094,806 B2 | 8/2006 | Nelson et al. | |
| 7,202,235 B2 | 4/2007 | Levy et al. | |
| 7,208,482 B2 | 4/2007 | Garcia-Luzon et al. | |
| 7,323,492 B2 | 1/2008 | Huss et al. | |
| 7,326,696 B2 | 2/2008 | Nelson et al. | |
| 7,361,674 B2 | 4/2008 | Nelson et al. | |
| 7,414,041 B2 | 8/2008 | Levy | |

(Continued)

FOREIGN PATENT DOCUMENTS

DE 2346535 A1 4/1974
WO 2004/091513 A2 10/2004

(Continued)

OTHER PUBLICATIONS

Arbeit et al., "Safety and Efficacy of PTK 0796: Results of the Phase 2 Study in Complicated Skin and Skin Structure Infections Following IV and Oral Step Down Therapy," Abstract L-1515b, Session 126, ICAAC, ASM Society, 2008.

Berge et al., "Pharmaceutical Salts," J. Pharm. Sci., 66(1):1-19 (1977).

Bhatia et al., "Activity of BAY 73-7388, a Novel Aminomethylcycline, and Other Novel Antibiotic Classes Against Resistant Bacteria In Vitro," Poster P925, ECCMID, ESCMID, 2004.

Bhatia et al., "PTK 0796 (BAY 73-6944) and other Novel Tetracycline Derivatives Exhibiting Potent In vitro and In vivo Activities Against Antibiotic Resistant Gram-Positive Bacteria," Abstract 2420, Poster F-755, ICAAC, ASM Society, 2003.

(Continued)

*Primary Examiner* — Shengjun Wang
(74) *Attorney, Agent, or Firm* — McCarter & English, LLP; Elizabeth A. Hanley; Yu Lu

(57) ABSTRACT

Methods and compositions for using a tetracycline compound to treat bacterial infections are described. In one embodiment, for example, the invention provides a method of treating a subject for an infection, comprising administering to said subject an effective amount of 9-[(2,2-dimethyl-propyl amino)-methyl]-minocycline or a salt thereof, such that said subject is treated, wherein said infection is selected from the group consisting of MSSA, MRSA, B-streptococci, Viridans *Streptococci, Enterococcus*, or combinations thereof.

20 Claims, No Drawings

(56) References Cited

U.S. PATENT DOCUMENTS

| | | | |
|---|---|---|---|
| 7,521,437 | B2 | 4/2009 | Nelson et al. |
| 7,553,828 | B2 | 6/2009 | Nelson et al. |
| 9,265,740 | B2 * | 2/2016 | Johnston ............... A61K 31/65 |
| 2003/0069721 | A1 | 4/2003 | Podlogar |
| 2004/0063674 | A1 | 4/2004 | Levy et al. |
| 2004/0138183 | A1 | 7/2004 | Nelson et al. |
| 2004/0176334 | A1 | 9/2004 | Nelson et al. |
| 2004/0214800 | A1 | 10/2004 | Levy et al. |
| 2004/0214801 | A1 | 10/2004 | Nelson et al. |
| 2004/0242548 | A1 | 12/2004 | Draper et al. |
| 2005/0020545 | A1 | 1/2005 | Draper et al. |
| 2005/0038002 | A1 | 2/2005 | Nelson et al. |
| 2005/0070510 | A1 | 3/2005 | Draper et al. |
| 2005/0143352 | A1 | 6/2005 | Nelson et al. |
| 2005/0250744 | A1 | 11/2005 | Levy et al. |
| 2005/0288262 | A1 | 12/2005 | Bandarage et al. |
| 2006/0003971 | A1 | 1/2006 | Nelson |
| 2006/0084634 | A1 | 4/2006 | Huss et al. |
| 2006/0089336 | A1 | 4/2006 | Nelson et al. |
| 2006/0166944 | A1 | 7/2006 | Berniac et al. |
| 2006/0166945 | A1 | 7/2006 | Abato et al. |
| 2006/0166946 | A1 | 7/2006 | Nelson et al. |
| 2006/0194773 | A1 | 8/2006 | Levy et al. |
| 2006/0281717 | A1 | 12/2006 | Berniac et al. |
| 2006/0287283 | A1 | 12/2006 | Amoo et al. |
| 2007/0072834 | A1 | 3/2007 | Nelson et al. |
| 2007/0093455 | A1 | 4/2007 | Abato et al. |
| 2007/0167415 | A1 | 7/2007 | Levy et al. |
| 2007/0270389 | A1 | 11/2007 | Garcia-Luzon et al. |
| 2008/0015169 | A1 | 1/2008 | Nelson et al. |
| 2008/0070873 | A1 | 3/2008 | Alekshun et al. |
| 2008/0118979 | A1 | 5/2008 | Draper et al. |
| 2008/0167273 | A1 | 7/2008 | Nelson et al. |
| 2008/0287401 | A1 | 11/2008 | Johnston et al. |
| 2008/0300424 | A1 | 12/2008 | Nelson et al. |
| 2008/0306032 | A1 | 12/2008 | Nelson et al. |
| 2008/0312193 | A1 | 12/2008 | Assefa et al. |
| 2009/0054379 | A1 | 2/2009 | Huss et al. |
| 2009/0118269 | A1 | 5/2009 | Berniac et al. |
| 2009/0124583 | A1 | 5/2009 | Nelson et al. |
| 2009/0131696 | A1 | 5/2009 | Levy |
| 2009/0156842 | A1 | 6/2009 | Seyedi et al. |
| 2009/0253660 | A1 | 10/2009 | Johnston |
| 2009/0306022 | A1 | 12/2009 | Nelson et al. |
| 2010/0022483 | A1 | 1/2010 | Berniac et al. |

FOREIGN PATENT DOCUMENTS

| | | | |
|---|---|---|---|
| WO | 2007/133797 | A2 | 11/2007 |
| WO | 2007/133798 | A2 | 11/2007 |
| WO | 2008/045507 | A2 | 4/2008 |
| WO | 2008/079339 | A2 | 7/2008 |
| WO | 2009/120389 | A1 | 10/2009 |
| WO | 2009/143509 | A1 | 11/2009 |

OTHER PUBLICATIONS

Broetz-Oesterhelt et al., "Superior Efficacy of BAY 73-7388, a Novel Aminomethylcycline, Compared with Linezolid and Vancomycin in Murine Sepsis Caused by Susceptible or Multiresistant Staphylococci," Poster P930, ECCMID, ESCMID, 2004.

Cannon et al., "Pharmacokinetics of PTK 0796 (BAY 73-6944) in Mouse, Rat and Cynomolgus Monkey," Abstract 2655, Poster F-759, ICAAC, ASM Society, 2003.

Chaturvedi et al., "In Vitro Assessment of Plasma Protein Binding and Metabolic Stability of PTK 0796 (BAY 73-6944)," Abstract 2675, Poster F-760, ICAAC, ASM Society, 2003.

Craig et al., "In Vivo Pharmacodynamics of MK-2764 / PTK 0796 Against Various Gram-positive and Gram-negative Bacteria in the Thighs of Neutropenic and Normal Mice," Abstract 1875, Poster F1-1974, ICAAC, ASM Society, 2006.

DuBois and Tanaka, "In Vitro Activity of MK-2764 / PTK 0796 Against *Legionella* spp.," Abstract 1846, Poster F1-1972, CAAC, ASM Society, 2006.

Endermann et al., "BAY 73-7388 is Highly Efficacious in Animal Models of Intraabdominal Infections Caused by a Range of Aerobic and Anaerobic Organisms, Including VRE," Poster P928, ECCMID, ESCMID, 2004.

Endermann et al., "BAY 73-7388, a Novel Aminomethylcycline, Is Highly Active In Vivo in a Murine Model of Pneumococcal Pneumonia," Poster P931, ECCMID, ESCMID, 2004.

Gorwitz et al. "Strategies for Clinical Management of MRSA in the community: Summary of an Experts' Meeting Convened by the Centers for Disease Control and Prevention," Mar. 2006, Centers for Disease Control and Prevention, <http://www.cdc.gov/ncidod/dhqp/ar_mrsa_ca.html>.

Ilyukevich et al., "Zivox (Linesolid)—Polyresistant Gram Positive Infections in ICU Finest Solution," Medicine, 1.52:38-41 (2006) (Russian Original and English Abstract).

Ladel et al., "BAY 73-7388 Demonstrates Greater Activity than Linezolid in a Range of Murine Models of Skin and Soft-Tissue Infection," Poster P929, ECCMID, ESCMID, 2004.

Macone et al. "In vitro Activity of PTK0796 Against Gram-Positive and Gram-Negative Organisms," Abstracts of Interscience of Conference on Antimicrobial Agents and Chemotherapy, 43:237 (2003).

Macone et al., "In Vitro Activity of PTK 0796 (BAY 73-6944) Against Gram-Positive and Gram-Negative Organisms," Abstract 2439, Poster F-754, ICAAC, ASM Society, 2003.

Macone et al., "Potent activity of BAY 73-7388, a Novel Aminomethylcycline, Against Susceptible and Resistant Gram-Positive and Gram-Negative Organisms," Poster P926, ECCMID, 2004.

McKenney et al., "BAY 73-7388, a Novel Aminomethylcycline, Exhibits Potent Efficacy in Pulmonary Murine Models of Infection," Poster P927, ECCMID, ESCMID, 2004.

McKenney et al., "Evaluation of PTK 0796 (BAY 73-6944) in Experimental Models of Infections Caused by Gram-Positive and Gram-Negative Pathogens," Abstract 2627, Poster F-757, ICAAC, ASM Society, 2003.

McKenney et al., "The Efficacy of PTK 0796 (BAY 73-6944) in Murine Models of *Streptococcus pneumoniae* Infections," Abstract 2637, Poster F-758, ICAAC, ASM Society, 2003.

Nilges et al., "Identification and Characterization of a Tetracycline Semiquinone Formed during the Oxidation of Minocycline," J. Org. Chem., 56:5623-5630 (1991).

Noel et al., "A Randomized, Evaluator-Blind, Phase 2 Study Comparing the Safety and Efficacy of Omadacycline to Those of Linezolid for Treatment of Complicated Skin and Skin Structure Infections," Antimicrob. Agents & Chemother., 56(11):5650-5654 (2012).

Smith et al., "Antistaphylococcal Activity of MK-2764 / PTK 0796 Compared to Other Agents," Abstract 1860, Poster F1-1971, ICAAC, ASM Society, 2006.

Tessier et al., "Pharmacokinetic/Pharmacodynamic Profile of MK-2764 / PTK 0796 against *S. pneumoniae* in a Murine Pneumonia Model," Abstract 1888, Poster F1-1973, ICAAC, ASM Society, 2006.

Traczewski and Brown, "PTK 0796 (BAY 73-6944): Effects of Environmental Variation on MICs and Confirmation of Disk Mass," Abstract 2463, Poster F-756, ICAAC, ASM Society, 2003.

Traczewski and Brown, "PTK 0796 (BAY 73-6944): In Vitro Potency and Spectrum of Activity Compared to Ten Other Antimicrobial Compounds," Abstract 2458, Poster F-753, ICAAC, ASM Society, 2003.

Weir et al., "The Activity of PTK 0796 (BAY 73-6944) Against Tetracycline Resistance," Abstract 2611, Poster F-752, ICAAC, ASM Society, 2003.

Weir et al., "The Mechanism of Action of PTK 0796 (Bay 73-6944)," Abstract 2473, Poster F-751, ICAAC, ASM Society, 2003.

* cited by examiner

MINOCYCLINE COMPOUNDS AND METHODS OF USE THEREOF

RELATED APPLICATIONS

This application is a continuation of U.S. patent application Ser. No. 14/258,847, filed on Apr. 22, 2014 and published as US 2015-0087711 A1; which is a continuation of U.S. patent application Ser. No. 12/398,980, filed on Mar. 5, 2009, now abandoned; which claims the benefit of the filing date under 35 U.S.C. 119(e) to U.S. Provisional Application Ser. No. 61/068,180, filed on Mar. 5, 2008, entitled "Methods of Treating Infectious Using Tetracycline Compounds." The entire contents of each of the foregoing applications are incorporated herein by reference.

BACKGROUND

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of minocycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced minocycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and *Salmonella*). The rise of tetracycline-resistant organisms has resulted in a general decline in use of tetracyclines and tetracycline analogue compositions as antibiotics of choice. In addition, other antibacterial agents have also been over used creating strains of multiple drug resistant bacteria.

Therefore, there is a need for effective antibacterial agents for the treatment of bacterial infections.

SUMMARY OF THE INVENTION

In one embodiment, the invention pertains, at least in part, to a method of treating a subject, comprising administering to the subject an effective amount of 9-[(2,2-dimethyl-propyl amino)-methyl]-minocycline or a salt thereof, wherein said tetracycline compound has an efficacy greater than linezolid for the treatment of bacterial infections.

In another embodiment, the invention also pertains, at least in part, to a method of treating a subject for an infection, by administering to the subject an effective amount of 9-[(2,2-dimethyl-propyl amino)-methyl]-minocycline or a salt thereof; wherein the tetracycline compound has a clinical success rate of about 93.7% or greater for treating infections of methicillin-susceptible *Staphylococcus aureus* (MSSA), methicillin-resistant *Staphylococcus aureus* (MRSA), B-streptococci, gram-negative bacteria (e.g., gram-negative rods (GNR)), Viridans *Streptococci*, *Enterococcus*, gram-positive bacteria (e.g., gram-positive anaerobes), or combinations thereof.

In another embodiment, the invention also pertains to a method of treating a subject for an infection, comprising administering to said subject an effective amount of 9-[(2,2-dimethyl-propyl amino)-methyl]-minocycline or a salt thereof, such that said subject is treated, wherein said infection is selected from the group consisting of MSSA, MRSA, B-streptococci, Viridans *Streptococci*, *Enterococcus*, and combinations thereof.

In another embodiment, said salt is a hydrochloride salt. In another embodiment, said salt is a tosylate salt.

In another embodiment, said subject is a human. In another embodiment, said subject is suffering from injury, abscess, ulcer, or cellulitis. In another embodiment, said injury is a trauma, surgery, bite, or burn.

In another embodiment, said 9-[(2,2-dimethyl-propyl amino)-methyl]-minocycline is administered orally. In another embodiment, said 9-[(2,2-dimethyl-propyl amino)-methyl]-minocycline is administered intravenously.

In another embodiment, said 9-[(2,2-dimethyl-propyl amino)-methyl]-minocycline is administered orally at dose of about 100 mg to about 300 mg per day. In another embodiment, said 9-[(2,2-dimethyl-propyl amino)-methyl]-minocycline is administered orally at a dose of about 200 mg per day. In another embodiment, said 9-[(2,2-dimethyl-propyl amino)-methyl]-minocycline is administered intravenously at a dose of about 50 mg to about 150 mg per day. In another embodiment, said 9-[(2,2-dimethyl-propyl amino)-methyl]-minocycline is administered intravenously at a dose of about 100 mg per day.

In another embodiment, said 9-[(2,2-dimethyl-propyl amino)-methyl]-minocycline has a clinical success rate of treating an infection of greater than about 93.2%. In another embodiment, said 9-[(2,2-dimethyl-propyl amino)-methyl]-minocycline has a microbiologically evaluable clinical success rate of treating an infection of greater than about 93.7%.

In another embodiment, the present invention provides a method of treating a subject for an infection, comprising administering to said subject an oral dose of about 100 mg to about 300 mg per day of 9-[(2,2-dimethyl-propyl amino)-methyl]-minocycline or a salt thereof, such that said subject is treated, wherein said infection is selected from the group consisting of MSSA, MRSA, B-streptococci, Viridans *Streptococci*, *Enterococcus*, and combinations thereof, and further wherein said subject is in need of treatment thereof.

In another embodiment, the present invention provides a method of treating a subject for an infection, comprising administering to said subject an intravenous dose of about 50 mg to about 150 mg per day of 9-[(2,2-dimethyl-propyl amino)-methyl]-minocycline or a salt thereof, such that said subject is treated, wherein said infection is selected from the group consisting of MSSA, MRSA, *B-streptococci*, Viridans *Streptococci, Enterococcus*, and combinations thereof, and further wherein said subject is in need of treatment thereof.

In another embodiment, the present invention provides a pharmaceutical composition comprising from about 100 to about 300 mg of 9-[(2,2-dimethyl-propyl amino)-methyl]-minocycline or a salt thereof and a pharmaceutically acceptable carrier for oral administration. In another embodiment, said composition comprises about 200 mg of said 9-[(2,2-dimethyl-propyl amino)-methyl]-minocycline.

In another embodiment, the present invention provides a pharmaceutical composition comprising from about 50 to about 150 mg of 9-[(2,2-dimethyl-propyl amino)-methyl]-minocycline or a salt thereof and a pharmaceutically acceptable carrier for intravenous administration. In another embodiment, said composition comprises about 100 mg of said 9-[(2,2-dimethyl-propyl amino)-methyl]-minocycline.

DETAILED DESCRIPTION OF THE INVENTION

The invention pertains, at least in part, to the discovery that 9-[(2,2-dimethyl-propyl amino)-methyl]-minocycline is effective to treat bacterial infections, including methicillin-susceptible *Staphylococcus aureus* (MSSA), methicillin-resistant *Staphylococcus aureus* (MRSA), *B-streptococci*, gram-negative bacteria (e.g., gram-negative rods (GNR)), Viridans *Streptococci, Enterococcus*, gram-positive bacteria (e.g., gram-positive anaerobes), or combinations thereof. 9-[(2,2-dimethyl-propyl amino)-methyl]-minocycline (compound 1) is a potent antibiotic with a greater clinical success rate than linezolid (e.g., N-[[3-(3-fluoro-4-morpholinophenyl)-2-oxooxazolidin-5-yl]methyl]acetamide, Zyvox™). The structure of linezolid is:

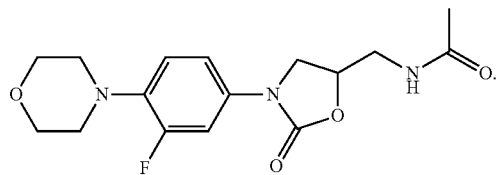 [SMILES: CC(=O)NCC1CN(c2ccc(N3CCOCC3)c(F)c2)C(=O)O1]

The invention pertains, at least in part, to a method of treating a subject, comprising administering to said subject an effective amount of compound 1 or a salt thereof, such that said subject is treated, wherein the tetracycline compound has an efficacy greater than linezolid.

The term "tetracycline compound" includes compounds with a four-ring core structure similar to that of tetracycline and its analogs (e.g., minocycline, sancycline, doxycycline, methacycline, etc.). The tetracycline compound of the invention is a 9-aminomethyl tetracycline compound, e.g., a compound substituted at the 9-position with an aminomethyl moiety (e.g., —CH$_2$—NR'R", wherein R' and R" can each be hydrogen, alkyl, alkenyl, alkynyl, cycloalkyl, aryl alkyl, etc.). The tetracycline compound is 9-[(2,2-dimethyl-propyl amino)-methyl]-minocycline (compound 1), or a salt thereof. The structure of compound 1 is:

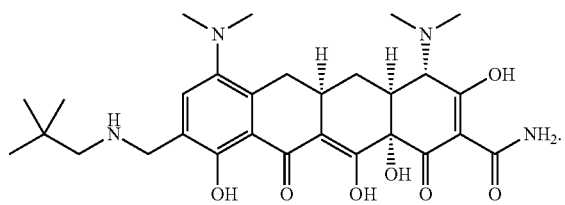 [SMILES: CN(C)c1cc(CNCC(C)(C)C)c(O)c2c1C[C@H]1C[C@H]3[C@H](N(C)C)C(O)=C(C(N)=O)C(=O)[C@@]3(O)C(O)=C1C2=O]

In a further embodiment, 9-[(2,2-dimethyl-propyl amino)-methyl]-minocycline is administered orally as the free base or as the tosylate salt. In another embodiment, 9[(2,2-dimethyl-propyl amino)-methyl]-minocycline is administered intravenously as the hydrochloride salt.

The term "treating" or "treatment" refers to the amelioration, eradication, or diminishment of one or more symptoms of the disorder, e.g., a bacterial infection, to be treated. In certain embodiments, the disorder term includes the eradication of bacteria associated with the infection to be treated.

The term "prophylaxis" means to prevent or reduce the risk of bacterial infection.

The term "resistance" or "resistant" refers to the antibiotic/organism standards as defined by the Clinical and Laboratories Standards Institute (CLSI) and/or the Food and Drug Administration (FDA).

In a further embodiment, the infection may be an infection caused by gram-positive pathogens (e.g., methicillin-susceptible *Staphylococcus aureus* (MSSA), methicillin-resistant *Staphylococcus aureus* (MRSA), *Enterococcus faecalis, Enterococcus faecium*, vancomycin-resistant *Enterococcus faecium* (VRE), *Streptococcus pneumoniae*, penicillin-resistant *Streptococcus pneumoniae* (PRSP), *Streptococcus pyogenes, Streptococcus agalactiae*, etc.), gram-negative pathogens (e.g., *Haemophilus influenzae, Moraxella catarrhalis, Neisseria gonorrhoeae, Escherichia coli, Shigella* spp., *Salmonella* spp., *Klebsiella pneumoniae, Enterobacter aerogenes, Enterobacter cloacae, Serratia marcescens, Acinetobacter baumannii, Stenotrophomonas maltophilia*, etc.), anaerobic pathogens (e.g., *Bacteroides fragilis, Clostridium perfringens*, etc.) and/or atypical pathogens (e.g., *Chlamydia pneumoniae, Legionella pneumophila*, etc.).

The infection may be resistant to other antibiotics, such as penicillin or tetracycline. Examples of bacterial infections which can be treated with the compounds of the invention include infections of MSSA, methicillin-resistant *Staphylococcus aureus* (MRSA) including both hospital-associated and community-associated MRSA, streptococci (e.g., *Streptococcus pneumoniae, Streptococcus pneumoniae* (PRSP), *Streptococcus pyogenes*, and *Streptococcus agalactiae*), gram-negative bacteria (e.g., gram-negative rods (GNR)), Viridans *Streptococci, Enterococcus*, gram-positive bacteria (e.g., gram-positive anaerobes), or combinations thereof.

In another embodiment, the infection is a hospital-associated MRSA infection. In another embodiment, the infection is a community-associated MRSA infection.

In another embodiment, the infection is an acute bacterial infection prompting or occurring during hospitalization.

In another embodiment, the present invention provides a method of treating a subject for an infection, comprising administering to said subject an effective amount of 9-[(2,2-dimethyl-propyl amino)-methyl]-minocycline or a salt thereof, such that said subject is treated, wherein said infection is selected from the group consisting of MSSA, MRSA, *B-streptococci*, Viridans *Streptococci, Enteroco-*

*cus*, mixed gram-positive cocci, mixed gram-positive cocci/ gram-negative rods or combinations thereof.

In another embodiment, the present invention provides a method of treating a subject for an infection, comprising administering to said subject an effective amount of 9-[(2, 2-dimethyl-propyl amino)-methyl]-minocycline or a salt thereof, such that said subject is treated, wherein said infection is selected from the group consisting of MSSA, MRSA, *B-streptococci*, mixed gram-positive cocci, mixed gram-positive cocci/gram-negative rods, or combinations thereof.

In another embodiment, the present invention provides a method of treating a subject for an infection, comprising administering to said subject an effective amount of 9-[(2, 2-dimethyl-propyl amino)-methyl]-minocycline or a salt thereof, such that said subject is treated, wherein said infection is selected from the group consisting of MSSA, MRSA, *B-streptococci*, or combinations thereof.

In another embodiment, the present invention provides a method of treating a subject for an infection, comprising administering to said subject an effective amount of 9-[(2, 2-dimethyl-propyl amino)-methyl]-minocycline or a salt thereof, such that said subject is treated, wherein said infection is selected from the group consisting of hospital-associated MRSA and community-associated MRSA.

In another further embodiment, the subject may be suffering from complicated skin and skin structure infections (CSSSI). Such CSSSI infections may result in hospitalization or occur during hospitalization.

In another further embodiment, the subject may be suffering from diabetic foot infections. Such diabetic foot infections may result in hospitalization or occur during hospitalization.

In another further embodiment, the subject may be suffering from community- or hospital-acquired pneumonia. Such community- or hospital-acquired pneumonia may result in hospitalization or occur during hospitalization.

In another further embodiment, the subject may be suffering from intra-abdominal infection. Such an intra-abdominal infection may result in hospitalization or occur during hospitalization.

In another further embodiment, the subject may be suffering from an injury (e.g., trauma, surgery, bite, removal of foreign body or burn), abscess (e.g., major or minor abscess), ulcer (e.g., lower or upper extremity ulcer), or cellulitis (which may be accompanied by a co-morbidity, such as diabetes mellitus, hepatitis C, substance abuse, cardiovascular disease (including coronary artery disease or peripheral vascular disease), vascular insufficiency, or immunosupressive therapy). Examples of major abscesses includes those which require drainage or involve subcutaneous or deeper tissues. An example of a burn includes a burn over less than 5% of the subject's body.

The term "subject" includes animals capable of suffering from a bacterial infection. Examples of subjects include animals such as farm animals (e.g., cows, pigs, horses, goats, rabbits, sheep, etc.), lab animals (mice, rats, etc.), pets (e.g., dogs, cats, ferrets, etc.), and primates (e.g., monkeys, gorillas, chimpanzees, and humans).

The tetracycline compound may be administered by any route which allows the compound to perform its intended function, e.g., treat a bacterial infection. Examples of routes include orally, intravenously, and topically. Preferably, the compound is administered orally or intravenously.

The term "effective amount" includes the amount of the tetracycline compound needed to treat a bacterial infection. For example, an effective amount describes an efficacious level sufficient to achieve the desired therapeutic effect through the killing of bacteria and/or inhibition of bacterial growth. Preferably, the bacterial infection is treated when the pathogen (e.g., bacteria) is eradicated.

The term "evaluable clinical success" refers to a clinical trial participant who:
(1) did not meet any criteria for evaluable clinical failure;
(2) did not receive potentially effective non-study antibiotics for any other reason; and
(3) the blinded evaluator indicated at the test of cure evaluation that the infection had sufficiently resolved such that antibiotics were not needed.

The term "evaluable clinical failure" refers to a clinical trial participant who met any one of the following criteria: the blinded evaluator discontinued study drug and indicated that the infection had responded inadequately such that alternative antibiotic(s) were needed; the blinded evaluator discontinued study drug because of an adverse event that was assessed as probably or possibly drug-related; the primary site of infection was surgically removed; or the subject had no evaluation after the end of intravenous treatment.

The term "clinical success rate" refers to the number of evaluable clinical successes divided by the total number of population in the trial.

The term "microbiologically evaluable clinical success rate" refers to those who met the definition of evaluable clinical success and had an infecting pathogen at baseline.

In one embodiment, the effective amount of the tetracycline compound, e.g. 9[(2,2-dimethyl-propyl amino)-methyl]-minocycline, when administered orally is from about 100 to about 300 mg, about 110 to about 290 mg, from about 120 to about 280 mg, from about 130 to about 270 mg, from about 140 to about 260 mg, from about 150 to about 250 mg, from about 160 to about 240 mg, from about 170 mg to about 230 mg, from about 180 mg to about 220 mg, from about 190 mg to about 210 mg, or about 200 mg. The compound may be administered as a salt (e.g., tosylate salt) or as a free base.

In another embodiment, the effective amount of the tetracycline compound, e.g., 9-[(2,2-dimethyl-propyl amino)-methyl]-minocycline, when administered intravenously is from about 50 to about 200 mg, from about 50 to about 150 mg, from about 60 to about 140 mg, from about 70 mg to about 130 mg, from about 80 mg to about 120 mg, from about 90 mg to about 110 mg, or about 100 mg.

It is to be understood that wherever values and ranges are provided herein, e.g., in ages of subject populations, dosages, and blood levels, all values and ranges encompassed by these values and ranges, are meant to be encompassed within the scope of the present invention. Moreover, all values in these values and ranges may also be the upper or lower limits of a range.

In another embodiment, the tetracycline compound may be administered once per day, either intravenously or orally.

In a further embodiment, the tetracycline compound has a greater clinical success rate than linezolid (e.g., N-[[3-(3-fluoro-4-morpholinophenyl)-2-oxooxazolidin-5-yl]methyl] acetamide), when the linezolid is administered at 600 mg orally or 600 mg intravenously every 12 hours.

In a further embodiment, the compound of the invention has a clinical success rate of greater than about 93.2%, greater than about 95%, greater than about 96%, greater than about 97%, or greater than about 98% when treating a bacterial infection. For example, a clinical success rate of about 93.7% or greater. Such bacterial infections include, e.g., MSSA, methicillin-resistant *Staphylococcus aureus*

(MRSA), B-streptococci, GNR, Viridans Streptococci, Enterococcus, gram-positive anaerobes, or combinations thereof. In contrast, linezolid was found to have a clinical success rate of 93.7% when treating infections of these bacteria.

In another further embodiment, the compound of the invention has a microbiologically evaluable clinical success rate of greater than about 93.7%, greater than about 95%, greater than about 96%, greater than about 97%, or about 97.4% or greater, when treating a bacterial infection. Such bacterial infections include, e.g., MSSA, methicillin-resistant Staphylococcus aureus (MRSA), B. streptococci, GNR, Viridans Streptococci, Enterococcus, gram-positive anaerobes, or combinations thereof.

In a further embodiment, the invention pertains to a method for treating a MSSA infection comprising administering an effective amount of an antibiotic compound, wherein said compound has a clinical success rate of greater than 91%. In a further embodiment, the antibiotic compound is a tetracycline compound, e.g., 9-[(2,2-dimethyl-propyl amino)-methyl]-minocycline. In contrast to linezolid which has a clinical success rate of 91% against MSSA (as determined in the trials described in the Exemplification of the Invention), 9-[(2,2-dimethyl-propyl amino)-methyl]-minocycline has a clinical success rate of 93% against MSSA.

In another further embodiment, the invention pertains to a method for treating a MRSA infection comprising administering an effective amount of an antibiotic compound, wherein said compound has a clinical success rate of greater than 93%. In a further embodiment, the antibiotic compound is a tetracycline compound, e.g., 9-[(2,2-dimethyl-propyl amino)-methyl]-minocycline. In contrast to linezolid which has a clinical success rate of 93% against MRSA (as determined in the trials described in the Exemplification of the Invention), 9-[(2,2-dimethyl-propyl amino)-methyl]-minocycline has a clinical success rate of 100% against MRSA.

In another further embodiment, the invention pertains to a method for treating a B. streptococci infection comprising administering an effective amount of an antibiotic compound, wherein said compound has a clinical success rate of greater than 0%, greater than 10%, greater than 20%, greater than 30%, greater than 50%, greater than 70%, greater than 80%, greater than 90%, greater than 91%, greater than 92%, greater than about 93%, greater than about 94%, greater than about 95%, greater than about 96%, greater than about 97%, greater than about 98%, greater than about 99%, or about 100%. In a further embodiment, the antibiotic compound is a tetracycline compound, e.g., 9[(2,2-dimethyl-propyl amino)-methyl]-minocycline. In contrast to linezolid which has a clinical success rate of 0% against B. streptococci (as determined in the trials described in the Exemplification of the Invention), 9-[(2,2-dimethyl-propyl amino)-methyl]-minocycline has a clinical success rate of 100% against B. streptococci.

In yet another further embodiment, the invention also pertains to a method of treating a subject for an infection. The method includes administering to the subject an effective amount of 9-[(2,2-dimethyl-propyl amino)-methyl]minocycline or salt thereof. Advantageously, the 9-[(2,2-dimethyl-propyl amino)-methyl]-minocycline has clinical success rate of about 93.7% or greater for treating infections. Examples of infections which can be treated using the methods of the invention include, but are not limited to, MSSA, MRSA, B-streptococci, GNR, Viridans Streptococci, Enterococcus, gram-positive anaerobes, or combinations thereof.

In a further embodiment, the salt is a tosylate salt or a free base when administered orally, or a hydrochloride salt when administered intravenously.

The invention also pertains, at least in part, to a method of treating a subject for an infection (e.g., a bacterial infection), by orally administering to said subject about 200 mg of 9-[(2,2-dimethyl-propyl amino)-methyl]-minocycline, tosylate salt, such that the subject is treated for the infection.

The invention also pertains, at least in part, to a method of treating a subject for an infection (e.g., a bacterial infection), by intravenously administering to the subject about 100 mg of 9-[(2,2-dimethyl-propyl amino)-methyl]-minocycline, hydrochloride salt, such that the subject is treated for the infection.

In another embodiment, the invention also pertains to a method of treating a subject for an infection (e.g., a bacterial infection), by orally administering to the subject about 200 mg of 9-[(2,2-dimethyl-propyl amino)-methyl]-minocycline, free base, such that the subject is treated for the infection.

In one example, a subject is treated intravenously followed by an oral step down. In another embodiment, the present invention provides a method of treating a subject for an infection, comprising administering to said subject an effective amount of compound 1 or a salt thereof wherein said subject is initially treated about 1 week or about 2 weeks or about 3 weeks intravenously followed by about 1 week or about 2 weeks or about 3 weeks of oral treatment, such that said subject is treated.

In another embodiment, the present invention provides a method of treating a subject for an infection, comprising administering to said subject an effective amount of compound 1 or a salt thereof wherein said subject initially treated intravenously has elevated compound 1 blood levels followed by reduced compound 1 blood levels with oral treatment, such that said subject is treated.

In another embodiment, the present invention provides a method of treating a subject for an infection, comprising administering to said subject an effective amount of compound 1 or a salt thereof for more than 28 days, up to and including about 28 days, up to and including about 21 days, up to and including about 14 days, up to and including about 10 days, up to and including about 9 days, up to and including about 8 days, or up to and including about 7 days, such that said subject is treated.

Pharmaceutical Compositions of the Invention

The invention also pertains to pharmaceutical compositions comprising a therapeutically effective amount of a tetracycline compound (e.g, a 9-aminomethyl tetracycline compound, e.g., 9-[(2,2-dimethyl-propyl amino)-methyl]-minocycline) or a salt thereof and, optionally, a pharmaceutically acceptable carrier.

In a further embodiment, the invention pertains to a pharmaceutical composition comprising from about 100 to about 300 mg of 9-[(2,2-dimethyl-propyl amino)-methyl]-minocycline or a salt there of and a pharmaceutically acceptable carrier. In a further embodiment, the pharmaceutically acceptable carrier is acceptable for oral administration. In another further embodiment, the tetracycline compound is a free base or a tosylate salt.

In yet another further embodiment, the composition comprises from about 110 to about 290 mg, from about 120 to about 280 mg, from about 130 to about 270 mg, from about 140 to about 260 mg, from about 150 to about 250 mg, from about 160 to about 240 mg, from about 170 mg to about 230 mg, from about 180 mg to about 220 mg, from about 190 mg to about 210 mg, or about 200 mg of 9-[(2,2-dimethyl-propyl amino)-methyl]-minocycline.

In another embodiment, the invention also pertains to a pharmaceutical composition comprising from about 50 to about 150 mg of 9-[(2,2-dimethyl-propylamino)-methyl]-minocycline or a salt thereof (e.g., a hydrochloride salt) and a pharmaceutically acceptable carrier suitable for intravenous administration.

In yet another further embodiment, the composition comprises from about 50 to about 150 mg, from about 60 to about 140 mg, from about 70 mg to about 130 mg, from about 80 mg to about 120 mg, from about 90 mg to about 110 mg, or about 100 mg of 9[(2,2-dimethyl-propyl amino)-methyl]-minocycline.

The language "pharmaceutically acceptable carrier" includes substances capable of being coadministered with the tetracycline compound of the invention, e.g., 9-[(2,2-dimethyl-propyl amino)-methyl]-minocycline, and which allow the tetracycline compound to perform its intended function, e.g., treat or prevent a bacterial infection. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the minocycline compounds of the invention that are basic in nature are those that form nontoxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a minocycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. Preferably, the tetracycline compound of the invention is administered as a tosylate (e.g., p-toluenesulfonate) salt or as a freebase orally or as a hydrochloride salt intravenously.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective tetracycline compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols.

When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic.

These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

EXEMPLIFICATION OF THE INVENTION

Example 1: Use of 9-[(2,2-dimethyl-propyl amino)-methyl]-minocycline to Treat Infections A randomized (1:1), controlled, evaluator-blinded Phase 2 study comparing 9-[(2,2-dimethyl-propyl amino)-methyl-minocycline (compound 1) and linezolid (Zyvox™) for the treatment of complicated skin and skin structure infections (CSSSI) was conducted. Patients with CSSSI who required initial intravenous (IV) therapy and met inclusion and exclusion criteria were enrolled at 11 centers in the US and were randomized to receive either compound 1 (100 mg Q24 h IV with 200 mg Q24 h oral step-down) or linezolid (600 mg Q12 h IV with 600 mg Q12 h oral step-down).

Study Evaluations

All subjects had four structured evaluations: at Enrollment (Baseline); at End of IV Treatment; at End of Treatment; and at 10 to 17 days after last dose of treatment (test of cure (TOC) evaluation). In addition, the blinded investigator saw each subject daily while they were on IV therapy and at least every 3 days while receiving oral treatment to determine whether to continue current treatment, switch from IV to oral therapy, or discontinue treatment.

At each of the four structured evaluations, the blinded evaluator assessed the subject, with particular attention to scoring the findings at the primary site of infection and obtaining cultures. Clinical and microbiologic outcomes were determined using these assessments. Primary evaluation criteria was safety and tolerability compared with linezolid. Secondary evaluation criteria was efficacy of compound 1 compared to linezolid, as well as pharmacokinetics of compound 1.

Subjects were randomized on a 1:1 basis to receive either compound 1 or linezolid. Random assignment of subjects avoids bias and helps ensure that both known and unknown risk factors are distributed evenly between treatment groups.

At each scheduled evaluation, the blinded evaluator examined the primary site of infection; for patients with multiple non-contiguous areas of infection, the blinded evaluator identified the most severely affected portion at Enrollment and designated that as the primary site of infection. The following information was recorded for each patient: maximal linear dimension of area of continuous involvement of infection; maximal linear dimension of ulceration, if present; semi-qualitative (scale of 0 to 3; none, mild, marked, severe) description of infection for the following features: erythema, edema/induration, fluctuance, necrotic tissue, purulence (including drainage), and tenderness/pain. In addition, at the Enrollment Evaluation, the following were also recorded the anatomical location of the primary site of infection; and the clinical diagnosis of the type of the infection.

In addition, the patients in the study were monitored for adverse events (AE). An adverse event is any untoward medical occurrence temporally associated with the use of a medical product in a subject, whether or not the event is considered causally related to the medical product. An AE can be a new occurrence or an existing process that increases significantly in intensity or frequency.

Patient Inclusion/Exclusion Criteria

Patients were between 18 and 80 years of age. Patients were on effective birth-control, or had no potential for childbearing. Patients had a qualifying infection (see below). Patients with any of the following conditions were not allowed in the trial: pregnant or nursing; previously treated under this protocol; non-qualifying skin/skin structure infection; allergy to study antibiotics; received investigational drug within one month; history of chronic liver cirrhosis; alanine aminotransferase (ALT) exceeding 2× upper limit of normal (ULN) during week prior to enrollment; total bilirubin exceeding ULN during week prior to enrollment; total body weight<40 kg or >150 kg; known to be HIV positive and meets CDC criteria for AIDS; life expectancy of less than 3 months; required hemodialysis or peritoneal dialysis; creatine clearance<30 mL/min; absolute neutrophil count<500/microliter; hypotension (supine systolic BP<90 mmHg) or perfusion abnormalities; required pressors to maintain blood pressure and/or adequate tissue perfusion; received potentially effective systemic antibiotic within 48 hrs; had an infecting pathogen know to be intermediate or resistant to study antibiotics; had confirmed or suspected non-infectious skin disorder that may potentially interfere with evaluations; or any concomitant condition that would interfere with evaluation or completion of the study.

Qualifying Infections

Examples of skin and soft tissue infections which were qualified to have been treated in the study were: Infections associated with trauma (e.g., traumatic injury (e.g., crush, puncture, laceration, gunshot)); surgical incisions; animal or human bites, providing the bite caused tissue damage; infections associated with removable foreign body (e.g., suppurative phlebitis associated with intravenous catheter sites, infected pacemaker pocket, etc.), and burns, second-degree involving <5% body surface), major abscesses (including carbuncles) which involve the subcutaneous or deeper tissues and require incision and drainage (or drained spontaneously), infected acute lower extremity ulcers with co-morbidity, wherein the ulcer is acute i.e., has been persistently present for less than three months, and is accompanied by at least one of the following diabetes mellitus requiring an oral hypoglycemic agent or insulin, arterial vascular insufficiency, or venous vascular insufficiency, or cellulitis with co-morbidity such as diabetes mellitus requiring an oral hypoglycemic agent or insulin, arterial vascular insufficiency; venous vascular insufficiency, or immunosuppressive therapy during the past 3 months.

Drug Administration

Both the investigational drug, compound 1, and the comparator drug, Zyvox™ were administered intravenously and orally. Patients randomized to linezolid may have received aztreonam IV for suspected or documented gram-negative infection. Subjects were initially treated with study drug IV and then switched to oral therapy. The expected duration of IV treatment was up to 7 days; the expected total duration of treatment (IV and oral) was up to 14 days.

For IV administration, the HCl salt of compound 1 for injection was given as 100 mg in 100 ml sterile saline infused over 30 minutes q24 h. For oral administration, compound 1 100 mg capsules were taken fasting as 2 capsules with 8 oz. water q24 h. No food was to be taken for 30 to 60 minutes after dosing and no dairy products for 4 hours.

Linezolid (Zyvox™) 600 mg tablets and pre-mixed 600 mg IV infusion solution (300 ml volume) were obtained from commercial sources. Linezolid 600 mg IV was administered as a 30 minute infusion.

Patients randomized to linezolid may have received aztreonam 2 g IV q 12 h for suspected or documented gram-negative infection. Aztreonam was obtained from commercial sources as a premixed infusion solution (2 g in 50 ml) and administered over 30 minutes. No other adjunct topical or systemic antibiotics were permitted.

Efficacy Analysis

Efficacy analyses were performed on several populations of subjects. Subjects were analyzed for efficacy according to randomization, regardless of treatment administered.

The Intent-to-Treat (ITT) population includes all enrolled subjects who received at least one dose of study medication.

The modified Intent-to-Treat (mITT) population comprises all subjects in the ITT population who have an Infecting Pathogen isolated at prior to administration of the study compound.

The Clinically Evaluable (CE) population comprises all subjects in the ITT population who meet specific criteria such that the clinical outcome of their infection could be inferred to reflect the effect of the study drug. The criteria include: have a qualifying skin and skin structure infection; receive the correct study drug (i.e., as randomized) for at least five calendar days, have the necessary clinical evaluations performed, and did not receive potentially confounding non-study antibiotics.

The Microbiologically Evaluable (ME) population includes all subjects in the CE population who had an infecting pathogen at baseline.

Subjects were considered to be an evaluable clinical failure if they meet any one of the following criteria: the blinded evaluator discontinued study drug and indicated that the infection had responded inadequately such that alternative antibiotic(s) were needed; the blinded evaluator discontinued study drug because of an adverse event that was assessed as probably or possibly drug-related; the primary site of infection was surgically removed; or the subject had no evaluation after the end of IV treatment.

Subjects were considered to be an evaluable clinical success if they meet all of the following: did not meet any criteria for evaluable clinical failure; did not receive potentially effective non-study antibiotics for any other reason; and at the test of cure evaluation the blinded evaluator indicates that the infection had sufficiently resolved such that antibiotics were not needed.

Pathogen Classification

An infecting pathogen was defined as an isolate derived from the last positive culture taken from the site of infection under study prior to and including day 1.

A persisting pathogen at the site of infection under study was defined as an isolate that was the same genus and species as an infecting pathogen; and was cultured at the Test-of-Cure evaluation from the site of infection under study.

A superinfecting pathogen at the site of infection under study is defined as a pathogen meeting all of the following criteria: represented a genus and species not isolated during the Enrollment evaluation, was cultured at any time from the day 3 of treatment to the test of cure evaluation, inclusive; was cultured from a patient who had at least one infecting pathogen; and was cultured from a patient who represents a "clinical failure."

A superinfecting pathogen at a site other than the infection under study is defined as a pathogen meeting all of the following criteria: represented a genus and species not isolated during the baseline evaluation; was cultured at any time from day 3 of treatment to the test of cure evaluation, inclusive; and was cultured from a patient who has an AE of infection at or related to the site from which the organism is cultured.

Microbiological Outcomes

Microbiological response to treatment was determined for each infecting pathogen using the following classification: documented eradication, presumed eradication, documented persistence, presumed persistence, or unknown.

Microbiological response to treatment was determined for each subject using the following classification:

Microbiologic Success—all infecting pathogens isolated at baseline were eradicated or presumed eradicated at the test-of-cure evaluation and no superinfecting pathogen was isolated from the site of infection under study.

Microbiological Failure—persistence or presumed persistence of one or more infecting pathogens or isolation of a superinfecting pathogen from the site of infection under study.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, issued patents, and published patent applications cited throughout this application are hereby incorporated by reference.

Results

Enrollment: 234 patients over 11 sites. No discontinuations due to elevated liver function tests (LFT)s. No serious adverse events (SAE)s. Interim data and safety monitoring board (DSMB)_review: no safety issues, blind not broken.

TABLE 1

Subpopulations.

| Subpopulations | Compound 1 | Linezolid |
|---|---|---|
| All randomized | 118 | 116 |
| Randomized, treated | 111 | 108 |
| Intent-to-treat | 111 (100%) | 108 (100%) |
| Modified ITT | 82 (73.9%) | 78 (72.2%) |
| Clinically evaluable | 100 (90.1%) | 88 (81.5%) |
| Microbiologically Evaluable | 75 (67.6%) | 63 (58.3%) |
| Safety Population | 111 (100%) | 108 (100%) |

TABLE 2

Demographics.

| Parameter | Demographic or Measure | Compound 1 (n = 111) | Linezolid (n = 108) |
|---|---|---|---|
| Sex | Female | 45 (40.5%) | 51 (47.2) |
|  | Male | 66 (59.5%) | 57 (52.8%) |
| Ethnicity | Hispanic | 38 (34.2%) | 53 (49.1%) |
|  | Non Hispanic | 73 (65.8%) | 55 (50.9%) |
| Race | Caucasian | 97 (87.4%) | 99 (91.7%) |
|  | Black | 8 (7.2%) | 6 (5.6%) |
|  | Asian | 4 (3.6%) | 1 (0.9%) |
|  | American Native | 0 | 1 (0.9%) |
|  | Other | 2 (1.8%) | 1 (0.9%) |
| Age (years) | 18-44 | 51 (45.9%) | 50 (46.3%) |
|  | 45-64 | 50 (45.0%) | 48 (44.4%) |
|  | >64 | 10 (9.0%) | 10 (9.3%) |
| Age | Mean | 44.9 | 45.8 |
|  | SD | 14.09 | 13.32 |
|  | Min | 19 | 19 |
|  | Median | 46 | 46 |
|  | Max | 81 | 76 |
| Weight | Mean | 84.2 | 85.0 |
|  | SD | 21.95 | 20.22 |
|  | Min | 45 | 51 |
|  | Median | 80 | 80 |
|  | Max | 144 | 152 |
| BMI (kg/m2) | Mean | 28.8 | 29.3 |
|  | SD | 6.89 | 6.80 |
|  | Min | 17 | 19 |
|  | Median | 28 | 28 |
|  | Max | 48 | 52 |

TABLE 3

Qualifying infections used in the study.

| Category | Compound 1 (n = 111) | Linezolid (n = 108) |
|---|---|---|
| Injury | 21 | 17 |
| Major Abscess | 73 | 72 |
| Lower extremity ulcer[1] | 9 | 9 |
| Cellulitis with co-morbidity[1] | 8 | 10 |

[1]14/18 LE ulcers and 11/18 cellulitis were in diabetics; most of the rest had venous insufficiency as co-morbidity.

TABLE 4

Maximal dimensions of infections (ITT population).

| Type of Infection | Compound 1 (n = 111)[a] | Linezolid (n = 108)[a] |
|---|---|---|
| Major Abscess[b] | 10 (6-16) | 7.8 (4.1-13) |
| Infected injury | 10.5 (4-31) | 7 (3-19.5) |
| Cellulitis with co-morbidity | 20 (12-31) | 18 (3.3-33) |

[a]Median (IQR) in centimeters
[b]Includes surrounding cellulitis
IQR = interquartile range

TABLE 5

Co-morbid conditions (ITT population).

| Condition[a] | Compound 1 (n = 111) | Linezolid (n = 108) |
|---|---|---|
| Hepatitis C seropositive | 46 (43%) | 40 (37%) |
| Substance abuse | 41 (37%) | 36 (33%) |
| Diabetes Mellitus | 27 (24%) | 20 (19%) |
| Cardiovascular Disease[b] | 35 (32%) | 38 (35%) |

[a]Hepatitis C seropositive confirmed by serology; other conditions based on patient medical histories
[b]Includes coronary artery or peripheral vascular disease

TABLE 6

Clinical findings.

| Characteristic | Measure | Compound 1 (n = 111) | Linezolid (n = 108) |
|---|---|---|---|
| Erythema | None | 1 (0.9%) | 2 (1.9%) |
|  | Mild | 10 (9.0%) | 21 (19.4%) |
|  | Moderate | 65 (58.6%) | 63 (58.3%) |
|  | Severe | 35 (31.5%) | 20 (18.5%) |
| Edema/Induration | None | 2 (1.8%) | 1 (0.9%) |
|  | Mild | 14 (12.6%) | 23 (21.3%) |
|  | Moderate | 63 (56.8%) | 57 (52.8%) |
|  | Severe | 32 (28.8%) | 25 (23.1%) |
| Purulence | None | 32 (28.8%) | 31 (28.7%) |
|  | Mild | 43 (38.7%) | 42 (38.9%) |
|  | Moderate | 28 (25.2%) | 28 (25.9%) |
|  | Severe | 8 (7.2%) | 5 (4.6%) |
| Tenderness/Pain | None | 1 (0.9%) | 0 |
|  | Mild | 8 (7.2%) | 10 (9.3%) |
|  | Moderate | 41 (36.9%) | 51 (47.2%) |
|  | Severe | 61 (55.0%) | 45 (41.7%) |
| Fluctuance | None | 53 (47.7%) | 53 (49.1%) |
|  | Mild | 28 (25.2%) | 27 (25.0%) |
|  | Moderate | 21 (18.9%) | 18 (16.7%) |
|  | Severe | 9 (8.1%) | 8 (7.4%) |
| Necrotic Tissue | None | 88 (79.3%) | 87 (80.6%) |
|  | Mild | 12 (10.8%) | 14 (13.0%) |
|  | Moderate | 9 (8.1%) | 5 (4.6%) |
|  | Severe | 2 (1.8%) | 0 |

TABLE 7

Subject disposition.

| Subject subpopulation | Compound 1 (n = 118) | Linezolid (n = 116) |
|---|---|---|
| Intent-to-treat | 111 | 108 |
| Completed Therapy | 106 (95.5%) | 100 (92.6%) |
| Premature Discontinuation | 5 (4.5%) | 8 (7.4%) |
| Adverse Event | 1 (0.9%) | 2 (1.9%) |
| Treatment Failure | 1 (0.9%) | 0 |
| Lost to follow-up | 3 (2.7%) | 6 (5.5%) |

TABLE 8

Duration of Treatment (ITT population).

| Route | Compound 1 (n = 111)[1] | Linezolid (n = 108)[1] |
|---|---|---|
| IV | 4 (2-6) | 3 (2-6) |
| Total (IV plus oral) | 10 (8-12) | 10 (7-13) |

[1]Median (IQR)

TABLE 9

Efficacy - ITT.

| Clinical Outcome | Compound 1 (n = 111) | Linezolid (n = 108) |
|---|---|---|
| Clinical Success | 98 (88.3%) | 82 (75.9%) |
| Clinical Failure | 13 (11.7%) | 26 (24.1%) |
| Failure | 2 (1.8%) | 6 (5.6%) |
| Nonevaluable | 11 (9.9%) | 20 (18.5%) |

TABLE 10

Efficacy - mITT.

| Clinical Outcome | Compound 1 (n = 84) | Linezolid (n = 78) |
|---|---|---|
| Clinical Success | 75 (89.3%) | 59 (75.6%) |
| Clinical Failure | 9 (10.7%) | 19 (24.4%) |
| Failure | 2 (2.4%) | 4 (5.1%) |
| Nonevaluable | 7 (8.3%) | 15 (19.2%) |

TABLE 11

Efficacy - clinically evaluable.

| Clinical Outcome | Compound 1 (n = 100) | Linezolid (n = 88) |
|---|---|---|
| Clinical Success | 98 (98.0%) | 82 (93.2%) |
| Clinical Failure | 2 (2.0%) | 6 (6.8%) |

TABLE 12

Efficacy - microbiologically evaluable.

| Clinical Outcome | Compound 1 (n = 77) | Linezolid (n = 63) |
|---|---|---|
| Clinical Success | 75 (97.4%) | 59 (93.7%) |
| Clinical Failure | 2 (2.6%) | 4 (6.3%) |

TABLE 13

Microbiology - mITT population.

| Bacteria | Primary Pathogen | Secondary Pathogen | Total Pathogens | Share of Primary (%) |
|---|---|---|---|---|
| MRSA | 82 | 0 | 82 | 51 |
| MSSA | 59 | 1 | 60 | 37 |
| Streptococci (beta and other) | 8 | 13 | 21 | 5 |
| Enterococci | 5 | 2 | 7 | 3 |
| Gram-negative rods | 5 | 16 | 21 | 3 |
| Anaerobes | 1 | 2 | 3 | 1 |
| Total | 160 | 34 | 194 | 100 |

TABLE 14

Distribution of baseline pathogen by treatment (mITT population).

| Bacteria | Compound 1 (n = 84) | Linezolid (n = 78) |
|---|---|---|
| MRSA | 44 (52.4%) | 38 (48.7%) |
| MSSA | 31 (36.9%) | 29 (37.2%) |
| B-hemolytic Streptococci | 7 (8.3%) | 2 (2.6%) |
| Streptococci, other | 4 (4.8%) | 8 (10.3%) |
| Enterococci | 2 (2.4%) | 5 (6.4%) |
| Gram-positive, other | 0 | 1 (1.3%) |
| Gram-negative, other | 13 (15.5%) | 8 (10.3%) |
| Anaerobes | 0 | 3 (3.8%) |

TABLE 15

Microbiology - clinical outcome (ME).

| | Compound 1 | | Linezolid | |
|---|---|---|---|---|
| Organism | Success (n = 73) | Failure (n = 2) | Success (n = 59) | Failure (n = 4) |
| MSSA | 27 | 2 | 21 | 2 |
| MRSA | 42 | 0 | 30 | 2 |
| B-Strep | 6 | 0 | 0 | 2 |
| GNR | 7 | 2 | 7 | 0 |
| Viridans Strep | 3 | 1 | 6 | 0 |
| Enterococcus | 1 | 1 | 3 | 0 |
| G+ anaerobes | 0 | 0 | 3 | 0 |
| Mixed GPC | 16 | 2 | 9 | 2 |
| Mixed GPC/GNR | 12 | 2 | 10 | 0 |

TABLE 16

Microbiology outcome (ME).

| Outcome[1] | Compound 1 (n = 75) | Linezolid (n = 63) |
|---|---|---|
| Presumed Eradication | 71 (94.7%) | 58 (92.1%) |
| Presumed Persistence | 2 (2.7%) | 4 (6.3%) |
| Persistence[2] | 2 (2.7%) | 1 (1.6%) |

[1]Presumed Eradication: Clinical success, no pathogen at TOC
Presumed Persistence: Clinical failure, no pathogen at TOC
Persistence: Clinical success, enrollment pathogen isolated at TOC
[2]MRSA persisted in all three cases

TABLE 17

Safety and adverse events (AE) by patient.

| | Compound 1 (n = 111) | | Linezolid (n = 108) | |
|---|---|---|---|---|
| Organ System | Total | Drug Related[a] | Total | Drug Related[a] |
| Cardiac | 4 | 0 | 4 | 3 |
| Ear | 0 | 0 | 2 | 1 |
| Eye | 2 | 0 | 1 | 1 |
| GI | 21 | 12 | 21 | 13[b] |
| General | 11 | 5 | 8 | 4 |
| Heme | 1 | 0 | 2 | 0 |
| Infection | 6 | 0 | 9 | 1 |
| Injury | 1 | 0 | 1 | 1 |
| Investigations | 7 | 3 | 11 | 8 |
| Metabolism | 9 | 1 | 7 | 2 |
| Musculoskeletal | 8 | 0 | 2 | 0 |
| Neurologic | 12 | 4 | 15 | 7 |
| Psych | 5 | 2 | 6 | 3 |
| Renal | 2 | 1 | 2 | 0 |
| Reproductive | 2 | 0 | 1 | 0 |
| Respiratory | 3 | 0 | 2 | 0 |
| Skin | 12 | 7 | 10 | 6[c] |
| Vascular | 3 | 0 | 1 | 1 |

TABLE 17-continued

Safety and adverse events (AE) by patient.

| | Compound 1 (n = 111) | | Linezolid (n = 108) | |
|---|---|---|---|---|
| Organ System | Total | Drug Related[a] | Total | Drug Related[a] |
| None | 65 (58.6%) | — | 53 (49.1%) | — |
| Total Patients with 1 or more AE | 56 (41.4%) | — | 55 (50.9%) | — |

[a]Assessed as probably or possibly drug-related by blinded evaluator
[b]Includes 1 patient discontinued due to heartburn
[c]Includes 1 patient discontinued due to rash

TABLE 18

Safety: ALT (max on treatment).

| | ALT Level | Compound 1 | Linezolid |
|---|---|---|---|
| ALT within normal limits at enrollment | Within normal limits | 84 (86.6%) | 75 (78.9%) |
| | 1x-2x | 12 (12.4%) | 14 (14.7%) |
| | 2x-3x | 0 | 5 (5.3%) |
| | >3x | 1 (1.0%) | 1 (1.1%) |
| ALT abnormal at enrollment[1] | Within normal limits | 1 (7.1%) | 2 (16.7%) |
| | NS | 11 (78.6%) | 8 (66.7%) |
| | Increase | 2 (14.3%) | 2 (16.7%) |

[1]NS: >ULN and <2x baseline.
Increase: >2x ULN and 2x baseline
NS = Not significant

TABLE 19

Safety: ALT (EOT).

| | ALT Level | Compound 1 | Linezolid |
|---|---|---|---|
| ALT within normal limits at enrollment | Within normal limits | 86 (93.5%) | 79 (87.8%) |
| | 1x-2x | 6 (6.5%) | 9 (10.0%) |
| | 2x-3x | 0 | 1 (1.1%) |
| | >3x | 0 | 1 (1.1%) |
| ALT abnormal at enrollment[1] | Within normal limits | 2 (15.4%) | 4 (36.4%) |
| | NS | 11 (84.6%) | 7 (63.6%) |
| | Increase | 0 | 0 |

[1]NS: >ULN and <2x baseline.
Increase: >2x ULN and 2x baseline
EOT = end of treatment

TABLE 20

Safety: ALT (TOC).

| | ALT Level | Compound 1 | Linezolid |
|---|---|---|---|
| ALT within normal limits at enrollment | Within normal limits | 85 (94.4%) | 75 (94.9%) |
| | 1x-2x | 5 (5.6%) | 4 (5.1%) |
| | 2x-3x | 0 | 0 |
| | >3x | 0 | 0 |
| ALT abnormal at enrollment[1] | Within normal limits | 3 (23.1%) | 5 (41.7%) |
| | NS | 9 (69.2%) | 6 (50.0%) |
| | Increase | 1 (7.7%) | 1 (8.3%) |

[1]NS: >ULN and <2x baseline.
Increase: >2x ULN and 2x baseline

Total bilirubin was slightly elevated in 2 patients in each group.

Summary of Results.

The ITT populations (111 received compound 1, 108 received linezolid) were comparable in terms of enrollment criteria, disease severity, co-morbidities, and demographics. Mean duration of total treatment and of IV and oral therapy did not differ between compound 1 (9.9, 4.3, 5.6 days respectively) and linezolid (9.7, 4.3, 5.4 days, respectively). The efficacy (clinical success) of compound 1 was 88.3% for the ITT population compared to 75.9% for linezolid. In the clinically evaluable population, the clinical success rates were 98% and 93.2% for compound 1 and linezolid, respectively. Bacterial pathogens were cultured at baseline from ~74% of each treatment group; over 50% had MRSA. Among the microbiologically evaluable patients, there were 2 failures in the compound 1 group, none was associated with MRSA and 4 failures in the linezolid group, 2 of which were associated with MRSA. Compound 1 was well tolerated. There were no discontinuations due to adverse events (AEs) for compound 1 (vs 2 for linezolid) and no drug-related serious AE in either group. In both treatment groups the most common drug-related AEs were gastrointestinal (12 PTK vs 13 linezolid). GI events associated with compound 1 were observed almost entirely during oral therapy, were mild, and did not result in discontinuation of therapy. There were no observed differences between the treatment groups in hematology or serum chemistry parameters.

The invention claimed is:

1. A method of treating a human subject for complicated Skin and Skin Structure Infections, comprising intravenously administering to said subject an effective amount of 9-[(2,2-dimethyl-propyl amino)-methyl]-minocycline or a salt thereof, such that said subject is treated, wherein gastrointestinal (GI) adverse events (AEs) associated with treatment are mild.

2. The method of claim 1, wherein said salt is a hydrochloride salt.

3. The method of claim 1, wherein said salt is a tosylate salt.

4. The method of claim 1, wherein said subject is suffering from injury, major abscess, or cellulitis.

5. The method of claim 4, wherein said injury is a traumatic injury.

6. The method of claim 1, wherein said 9-[(2,2-dimethyl-propyl amino)-methyl]-minocycline is administered intravenously at a dose of about 50 mg to about 150 mg per day.

7. The method of claim 6, wherein said 9-[(2,2-dimethyl-propyl amino)-methyl]-minocycline is administered intravenously at a dose of about 100 mg per day.

8. The method of claim 1, wherein said 9-[(2,2-dimethyl-propyl amino)-methyl]-minocycline has a clinical success rate of treating an infection of greater than about 93.2%.

9. The method of claim 1, wherein said 9-[(2,2-dimethyl-propyl amino)-methyl]-minocycline has a microbiologically evaluable clinical success rate of treating an infection of greater than about 93.7%.

10. The method of claim 1, wherein said skin and skin structure infections are caused by *Staphylococcus aureus*, *Streptococci*, or a combination thereof.

11. The method of claim 10, wherein said *Staphylococcus aureus* is methicillin-resistant *Staphylococcus aureus* (MRSA), or methicillin-susceptible *Staphylococcus aureus* (MSSA).

12. The method of claim 10, wherein said *Streptococci* is beta *Streptococci*.

13. The method of claim 10, wherein said *Streptococci* is *Streptococcus pyogenes*.

14. The method of claim 1, wherein said skin and skin structure infections are characterized by the presence of one or more of erythema, edema, and induration.

15. The method of claim 1, wherein said 9-[(2,2-dimethyl-propyl amino)-methyl]-minocycline is administered once per day.

16. The method of claim 1, wherein said 9-[(2,2-dimethyl-propyl amino)-methyl]-minocycline is administered intravenously, followed by an oral administration.

17. The method of claim 16, wherein said subject is treated up to and including about 14 days, up to and including about 10 days, up to and including about 9 days, up to and including about 8 days, or up to and including about 7 days, such that said subject is treated.

18. The method of claim 16, wherein said 9-[(2,2-dimethyl-propyl amino)-methyl]-minocycline is administered intravenously by up to 7 days, followed by about 1 week or about 2 weeks of oral administration.

19. The method of claim 18, wherein said 9-[(2,2-dimethyl-propyl amino)-methyl]-minocycline is administered intravenously for about 4 days, and total treatment period including intravenous and oral administration is about 10 days.

20. The method of claim 1, wherein GI adverse events (AEs) associated with treatment do not result in discontinuation of therapy.

\* \* \* \* \*